United States Patent [19]

De Labbey et al.

[11] Patent Number: 5,053,053

[45] Date of Patent: Oct. 1, 1991

[54] PROCESS FOR DYEING KERATINOUS FIBRES WITH A HYDROXYINDOLE IN COMBINATION WITH A QUINONE DERIVATIVE; AND NOVEL 1,4-BENZOQUINONES

[75] Inventors: Arnaud De Labbey, Aulnay-sous-Bois; Alain Baudry, Gonesse; Daniel Bauer, Le Raincy; Pierre Bore, Montfermeil, all of France

[73] Assignee: L'Oreal, Paris, France

[21] Appl. No.: 446,544

[22] Filed: Dec. 6, 1989

[30] Foreign Application Priority Data

Dec. 6, 1988 [LU] Luxembourg ............................ 87403

[51] Int. Cl.$^5$ ...................... A61K 7/13; C07C 323/08; D06M 3/00; D06P 3/08
[52] U.S. Cl. ............................................. 8/423; 8/405; 8/406; 8/407; 8/408; 8/429; 552/293
[58] Field of Search .................. 8/423, 408, 409, 429

[56] References Cited

U.S. PATENT DOCUMENTS

| | | |
|---|---|---|
| 3,328,301 | 6/1967 | Thompson et al. ............... 252/47.5 |
| 3,516,778 | 6/1970 | Brunner ................................. 8/405 |
| 3,929,404 | 12/1975 | Kalopissis et al. ................... 8/407 |
| 4,045,170 | 8/1977 | Kalopissis et al. ................... 8/416 |
| 4,046,786 | 9/1977 | Kalopissis et al. ................... 8/416 |
| 4,054,147 | 10/1977 | Kalopissis et al. ................... 8/416 |
| 4,093,806 | 6/1978 | Kalopissis et al. ................... 544/165 |
| 4,804,385 | 2/1989 | Grollier et al. ....................... 8/423 |
| 4,808,190 | 2/1989 | Grollier et al. ....................... 8/423 |
| 4,822,375 | 4/1989 | Lang et al. ........................... 8/423 |
| 4,867,751 | 9/1989 | Lang et al. ........................... 8/405 |
| 4,885,006 | 12/1989 | Grollier et al. ....................... 8/423 |
| 4,888,027 | 12/1989 | Grollier et al. ....................... 8/423 |

FOREIGN PATENT DOCUMENTS

| | | |
|---|---|---|
| 3930446 | 3/1990 | Fed. Rep. of Germany . |
| 2110722 | 6/1983 | United Kingdom . |
| 2187456 | 9/1987 | United Kingdom . |
| 2214526 | 9/1989 | United Kingdom . |

OTHER PUBLICATIONS

Tetrahedron, vol. 43, No. 12, 1987, pp. 2749–2754, A. Napolitano et al.; "A Reinvestigation of the Reactions Between 5,6–Dihydroxyindoles and Quinones".
Tetrahedron Letters, vol. 25, No. 42, pp. 4833–4836, 1984, Warrener et al.
J. Org. Chem. 1985, 50, 1963–1969, Hayakawa et al.
J. Electrochem. Soc.: Electrochemical Science, vol. 110, vol. 1, pp. 57–63, The Effect of Molecular Structure on the Electrode Kinetics of Aminoquinones and Quinone Thioethers.

*Primary Examiner*—A. Lionel Clingman
*Attorney, Agent, or Firm*—Cushman, Darby & Cushman

[57] ABSTRACT

Process for dyeing keratinous fibres, comprising the step of applying to these fibres at least one composition A containing, in a medium appropriate for dyeing, at least one mono- or di-hydroxyindole the application of the composition A being preceded or followed by the application of a composition B containing, in a medium appropriate for dyeing, at least one quinone derivative chosen from ortho- or para-benzoquinones, monoimines or diimines of ortho- or para-benzoquinones, 1,2- or 1,4-naphthoquinones, sulphonimides of ortho- or para-benzoquinones, α, ω-alkylene-bis-1,4-benzoquinones, or 1,2- or 1,4-naphthoquinone-monoimines or -diimines; the mono- or di-hydroxyindoles and the quinone derivatives being chosen such that the oxidation-reduction potential difference $\Delta E$ between the oxidation-reduction potential $E_i$ of the mono- or di-hydroxyindoles, determined at pH 7 in a phosphate medium on a vitreous carbon electrode by voltametry, and the oxidation-reduction potential $E_q$ of the quinone derivative determined at pH 7 in a phosphate medium by polarography on a mercury electrode and relative to a saturated calomel electrode is such that $$\Delta E = E_i - E_q \leq 320 \ mV.$$

19 Claims, No Drawings

PROCESS FOR DYEING KERATINOUS FIBRES WITH A HYDROXYINDOLE IN COMBINATION WITH A QUINONE DERIVATIVE; AND NOVEL 1,4-BENZOQUINONES

The present invention relates to a novel process for dyeing keratinous fibers, and more particularly human keratinous fibers, such as hair, using at least one hydroxyindole in combination with at least one quinone derivative and novel 1,4-benzoquinones.

Dyeing keratinous fibers and in particular hair with the aid of hydroxy derivatives of indole has already been proposed in the past, and more particularly in the French Patents Nos. 1,133,594, 1,166,172 and 2,390,158 and French Patent Application 2,536,993, which propose processes for dyeing with the aid of 5,6-dihydroxyindole using metal cations playing the role of melanogenesis promoter.

The process described in French Patent Application No. 2,594,331 company uses either manganese in the form of permanganate or a bichromate.

However, the use of metal cations in the dyeing processes presents a certain number of problems to the extent that it is relatively difficult to remove these metal cations from the hair.

After two treatments and despite rinsings, traces of metals always remain on the hair, which can present problems when the hair subsequently has to be subjected to treatments such as bleaching or permanent waves. This is in particular the case with copper and manganese.

There has, moreover, been described, in its French Patent Applications 2,593,061 and 2,593,062, a dyeing process using indole derivatives and more particularly 5,6-dihydroxyindole in combination with an inorganic anion and more particularly an iodide.

In this case, however, the processes necessitate the use of an inorganic oxidant, which is in particular hydrogen peroxide.

The dyeing of hair using hydroxyindole derivatives and oxidants, such as periodic acid and the periodates, potassium permanganate, sodium hypochlorite, potassium ferricyanide, potassium bichromate, ammonium persulphate, silver oxide, ferric chloride, lead oxide, calcium sulphate or Fenton's reagent, has also been described in the Application EP-A-271,186.

There has now been discovered, and it is this which is the subject of the invention, that it was possible, in a surprising manner, to carry out a dyeing with the aid of hydroxy derivatives of indole without using hydrogen peroxide, ammonia, a metal cation or an inorganic anion, by impregnating the keratinous fibers and in particular the hair with the hydroxy derivative of indole, this impregnation being preceded or followed by the application of a composition containing a quinone derivative.

The applicants have discovered, in particular, that it was particularly easy to dye natural hair in very diverse shades, from light hues to dark hues.

The subject of the invention is thus a novel process for dyeing keratinous fibers, and in particular human keratinous fibers, using a hydroxy derivative of indole and a quinone derivative as oxidizing agent.

Other subjects of the invention are multi-compartment devices used within the framework of this process.

Other subjects of the invention will become apparent on reading the description and the examples which follow.

The process for dyeing keratinous fibers, and in particular human keratinous fibers, such as hair, according to the invention, is essentially characterized by the fact that at least one composition (A) containing, in a medium appropriate for dyeing, at least one mono- or dihydroxyindole is applied to these fibers, the application of the composition (A) being preceded or followed by the application of a composition (B) containing, in a medium appropriate for dyeing, at least one quinone derivative chosen from ortho- or para-benzoquinones monoimines or diimines of ortho- or para-benzoquinones monoimines or diimines, sulphonimides of ortho- or para-benzoquinones, $\alpha,\omega$-alkylene-bis-1,4-benzoquinones, 1,2- or 1,4-naphthoquinones, and 1,2-1,4-naphthoquinone-monoimines or -diimines; the mono- or di-hydroxyindoles and the quinone derivatives being chosen such that the oxidation-reduction potential difference $\Delta E$ between the oxidation-reduction potential $E_i$ of the mono- or di-hydroxyindoles, determined at pH 7 in a phosphate medium on a vitreous carbon electrode by voltametry, and the oxidation-reduction potential $E_q$ of the quinone derivatives, determined at pH 7 in a phosphate medium by polarography on a mercury electrode and relative to a saturated calomel electrode, is such that $$\Delta E = E_i - E_q \leq 320 mV.$$

The mono- or di-hydroxyindoles used according to the invention correspond more particularly to the formula (I) below:

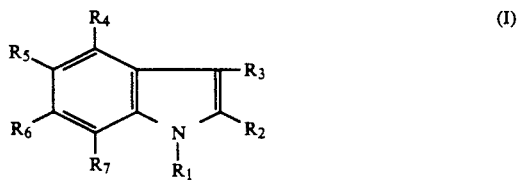

in which:

$R_1$ denotes hydrogen or a $C_1$–$C_4$-alkyl group;

$R_2$ and $R_3$, which may be identical or different, represent a hydrogen atom, a $C_1$–$C_4$-alkyl group, a carboxyl group or a $C_1$–$C_4$-alkoxycarbonyl, $C_1$–$C_4$-hydroxyalkyl or $C_1$–$C_4$-aminoalkyl group; and $R_4$, $R_5$, $R_6$ and $R_7$, independently of one another, represent a hydrogen atom, a $C_1$–$C_4$-alkyl radical, amino, which may be unsubstituted or substituted by one or two $C_1$–$C_4$-alkyl or -hydroxyalkyl groups, $C_2$–$C_6$-acylamino, carboxyl, $C_1$–$C_4$-carboxyalkyl, $C_1$–$C_4$-alkoxycarbonyl or

(where r and r' denote, independently of one another, hydrogen or $C_1$–$C_4$-alkyl), halogen, $C_1$–$C_4$-hydroxyalkyl, $C_1$–$C_4$-aminoalkyl, OH or OZ, Z denoting a linear or branched $C_1$–$C_{20}$-alkyl radical, an aralkyl group, a formyl group, a linear or branched $C_2$–$C_{20}$-acyl group, a linear or branched $C_3$–$C_{20}$-alkenyl group, a —$SiR_{11}R_{12}R_{13}$ group, a —$P(O)(OR_8)_2$ group or a $R_8O$-$SO_2$- group; the radicals $R_4$ and $R_5$, or $R_5$ and $R_6$, or $R_6$ and $R_7$ being able to form, together with the carbon atoms to which they are bonded, a ring which may contain a carbonyl group, a thiocarbonyl group, a

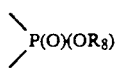

group or a

group with the proviso that at least one of the radicals $R_4$ to $R_7$ represents an OH group, $R_8$ and $R_9$ represent a hydrogen atom or a $C_1-C_4$-alkyl group, $R_{10}$ represents a $C_1-C_4$-alkoxy group or a $C_1-C_4$-monoalkyl- or -dialkyl-amino group, and $R_{11}$, $R_{12}$ and $R_{13}$, which may be identical or different, represent linear or branched $C_1-C_4$-alkyl groups, and the corresponding alkali metal, alkaline earth metal, ammonium and amine salts of these compounds.

In the above formula, the linear or branched $C_1-C_{20}$-alkyl radicals are chosen in particular from methyl, ethyl, propyl, butyl and hexadecyl; the aralkyl group is preferably a benzyl group; the $C_2-C_{20}$-acyl group is preferably chosen from the acetyl, propionyl, butanoyl, pivaloyl, hexanoyl, myristoyl and hexadecanoyl groups; the linear or branched $C_3-C_{20}$-alkenyl group is preferably chosen from the radicals butenoyl and oleyl.

The compounds particularly preferred, according to the invention, are chosen more particularly from:
4-hydroxyindole
4-hydroxy-5-methoxyindole
4-hydroxy-5-ethoxyindole
5-hydroxyindole
2-carboxy-5-hydroxyindole
5-hydroxy-6-methoxyindole
6-hydroxyindole
6-hydroxy-7-methoxyindole
5-methoxy-6-hydroxyindole
2-carboxy-6-hydroxyindole
2-ethoxycarbonyl-6-hydroxyindole
7-hydroxyindole
2,3-dimethyl-7-hydroxy-4-methoxyindole
5,6-dihydroxyindole
1-methyl-5,6-dihydroxyindole
2-methyl-5,6-dihydroxyindole
3-methyl-5,6-dihydroxyindole
2,3-dimethyl-5,6-dihydroxyindole
(5 or 6)-acetoxy-(6 or 5)-hydroxyindole
2-ethoxycarbonyl-5,6-dihydroxyindole
2-carboxy-5,6-dihydroxyindole
2,3-dimethyl-5-hydroxy-6-aminoindole
2,3-dimethyl-5-amino-6-hydroxyindole.

The quinone derivatives are chosen more particularly from the compounds corresponding to the formulae (II) and (II'):

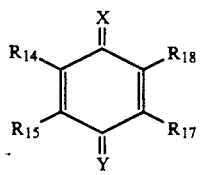 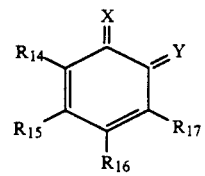

(II)   (II¹)

in which:
X denotes oxygen or a $NR_{19}$ group;
Y denotes oxygen or a $NR_{20}$ group;

$R_{19}$ and $R_{20}$, which may be identical or different denote hydrogen, halogen, a $C_1-C_4$-alkyl or $C_1-C_4$-hydroxyalkyl radical, a $C_1-C_4$-alkylsulphonyl radical or a phenylsulphonyl radical;

$R_{14}$, $R_{15}$, $R_{16}$, $R_{17}$ and $R_{18}$ denote, independently of one another, hydrogen, a $C_1-C_4$-alkyl radical, a carboxyl group, $C_1-C_4$-alkylcarbonyl, $C_1-C_4$-alkoxycarbonyl, $C_1-C_4$-alkoxy-methyl, $C_1-C_4$-alkyl-thiomethyl, $C_1-C_4$-hydroxyalkylthiomethyl, $C_1-C_4$-hydroxyalkylsulphinyl,

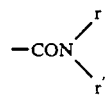

(r and r' denoting, independently of one another, hydrogen or $C_1-C_4$-alkyl), $C_1C_4$-carboxyalkyl, halogen, $C_1-C_4$-hydroxyalkyl, amino, which may be unsubstituted or substituted by one or two $C_1-C_4$-alkyl or -hydroxyalkyl groups, $C_2-C_6$-acylamino, $SO_3M$, where M denotes hydrogen, K or Na, sulphoxide, sulphone or sulphonamide, which may be substituted, or a radical $OZ_1$ in which $Z_1$ may be hydrogen, $C_1-C_4$-alkyl, $C_1-C_4$-hydroxyalkyl, $C_1-C_4$-carboxyalkyl or phenyl, which is optionally substituted by $C_1-C_4$-alkoxy, or a radical $-SZ_2$ in which $Z_2$ is a $C_1-C_4$-alkyl, $C_1-C_4$-hydroxyalkyl, $C_2-C_4$-dihydroxyalkyl or $C_1-C_4$-carboxyalkyl group;

$R_{14}$ and $R_{15}$ can form, with the carbon atoms to which they are attached, the following cyclic group:

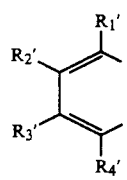

(III)

in which:
$R'_1$, $R'_2$, $R'_3$ and $R'_4$ have the meanings indicated above for $R_{14}$, $R_{15}$, $R_{16}$, $R_{17}$ and $R_{18}$ when these do not form a ring.

According to the invention, halogen is preferably chosen from fluorine, chlorine or bromine.

The invention also relates to novel benzoquinones of formula:

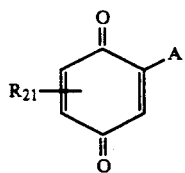

in which A represents the groups $CH_2SR$ or $SR$, in which R denotes a $C_1-C_4$-alkyl or $C_1-C_4$-hydroxyalkyl group; and $R_{21}$ represents a hydrogen atom, a $C_1-C_4$-alkyl radical or the group SR, R having the meaning mentioned above, with the proviso that $R_{21}$ represents a hydrogen atom when A denotes the group $-CH_2SR$, and their use in tinctorial compositions for keratinous fibers, such as hair.

The preferred compounds are chosen in particular from the benzoquinones of formulae (II) and (II'), in which:

$R_{14}$, $R_{15}$, $R_{16}$, $R_{17}$ and $R_{18}$ denote, independently of one another, hydrogen, $C_1-C_4$-lower alkyl, $C_1-C_4$-lower alkoxy, halogen, $C_2-C_6$-acylamino, $SO_3M$, $C_1-C_4$-alkoxy-emthyl, carboxy-$(C_1-C_4)$-alkyl, $C_1-C_4$-alkoxy-carbonyl, di-$(C_1-C_4)$-alkyl-amino, $OZ_1$ in which $Z_1$ represents carboxy-$(C_1-C_4)$-alkyl or $C_1-C_4$-hydroxyalkyl, or $SZ_2$ in which $Z_2$ represents $C_1-C_4$-hydroxyalkyl, dihydroxy-$(C_1-C_4)$-alkyl, carboxy-$(C_1-C_4)$-alkyl or $C_1-C_4$-alkyl;

X denotes oxygen or the group $NR_{19}$;

Y denotes oxygen or the group $NR_{20}$; and $R_{19}$ and $R_{20}$, independently of one another, denote hydrogen, halogen or $C_1-C_4$-lower alkyl methylsulphonyl or phenylsulphonyl.

Other preferred compounds used in accordance with the invention correspond to the formulae (V) and (VI) below:

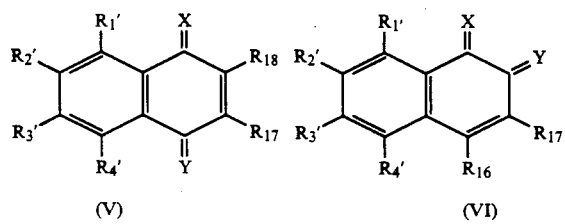

in which:

$R'_1$, $R'_2$, $R'_3$, $R'_4$, $R_{16}$, $R_{17}$ and $R_{18}$ have the meanings indicated above for the compounds of formulae (II), (II') and (III);

X and Y having the same meanings as those indicated above.

The particularly preferred compounds are chosen from those in which $R'_1$, $R'_2$, $R'_3$, $R'_4$, $R_{16}$, $R_{17}$ and $R_{18}$ denote hydrogen, $C_1-C_4$-alkyl, $C_1-C_4$-alkoxy, halogen, $C_2-C_6$-acylamino or $SO_3H$.

The particularly preferred compounds which can be used in accordance with the invention are, in particular:
1,4-benzoquinone
2-methoxy-1 4-benzoquinone
2-methyl-1,4-benzoquinone
2,6-dimethyl-1,4-benzoquinone
2,3,5-trichloro-6-methyl-1 4-benzoquinone
2-acetylamino-1,4-benzoquinone
2-acetylamino-3,5-dimethyl-1,4-benzoquinone
2,6-dimethyl-5-acetylamino-1 4-benzoquinone
2-chloro-1,4-benzoquinone
tetrachloro-1,2-benzoquinone
2,3-dimethoxy-1 4-benzoquinone
2-($\beta$-carboxyethoxy)-1,4-benzoquinone
2-methoxymethyl-1,4-benzoquinone
2-($\beta$-hydroxyethyl)-1,4-benzoquinone
2-($\beta$-hydroxyethylthio)-1,4-benzoquinone
2,5-bis-($\beta$-hydroxyethylthio)-1,4-benzoquinone
2-($\beta,\gamma$-dihydroxypropylthio)-1,4-benzoquinone
2-($\beta$-carboxyethylthio)-1,4-benzoquinone
2-carboxymethyl-1,4-benzoquinone
2-($\beta$-hydroxyethylthio)-6-methyl-1,4-benzoquinone
2-methoxycarbonyl-3-methoxy-1,4-benzoquinone
2-methoxycarbonyl-1,4-benzoquinone
2-methylthio-1,4-benzoquinone
2-dimethylamino-1,4-benzoquinone
2-acetylamino-5-methoxy-1 4-benzoquinone
2-($\beta$-hydroxyethylthio)methyl-1,4-benzoquinone
2-(methylthio)methyl-1 4-benzoquinone
4,5-dimethoxy-1,2-benzoquinone
4-methyl-5-chloro-1,2-benzoquinone
4,5-dimethyl-1,2-benzoquinone
2,3-dimethyl-1,4-benzoquinone
2-($\beta$-hydroxyethoxy)-1,4-benzoquinone
N-methylsulphonyl-1 4-benzoquinone monoimine
N-phenylsulphonyl-1,4-benzoquinone monoimine
1,4-naphthoquinone
1,2-naphthoquinone
1,2-naphthoquinone-4-sulphonic acid
2,3-dichloro-1,4-naphthoquinone
N-2,6-trichloro-1,4-benzoquinone imine.

The combinations particularly preferred, according to the invention, are chosen from the combination of 5,6-dihydroxyindole with 1,4-benzoquinone, 2-methyl-1,4-benzoquinone, 2,6-dimethyl-1,4-benzoquinone, 2-methoxy-1,4-benzoquinone, 2-chloro-1,4-benzoquinone, 2,3,5-trichloro-6-methyl-1,4-benzoquinone, 2-acetylamino-1,4-benzoquinone, 2-acetylamino-3-methoxy-1,4-benzoquinone, 2,6-dimethyl-5-acetylamino-1,4-benzoquinone, 2,3-dimethoxy-1,4-benzoquinone, 2-methoxymethyl-1,4-benzoquinone, 2-($\beta$-hydroxyethyl)-1,4-benzoquinone, 2-($\beta\gamma$-dihydroxypropylthio)-1,4-benzoquinone, 2-($\beta$-carboxyethylthio)-1,4-benzoquinone, 2-carboxymethyl-1,4-benzoquinone, 1,4-naphthoquinone, N-2,6-trichloro-1,4-benzoquinone imine, 1,2-naphthoquinone or 1,2-naphthoquinone-4-sulphonic acid.

Under the customary conditions for a dyeing, that is to say for exposure times of 2 to 30 minutes and a temperature customarily tolerated by the models, for example between 25° and 40° C, the concentration of the monohydroxyindole or of the dihydroxyindole used in the composition (A) is preferably between 0.01 and 0.3 mole/liter.

The concentration of quinone derivative is such that it permits the oxidation of the monohydroxyindole or dihydroxyindole under the conditions customarily used by the hairdresser during a dyeing and is preferably between 0.005 and 1 mole/liter in the composition (B).

The pH of the composition (A) is preferably between 2 and 10.

The pH of the composition (B) is preferably between 2 and 10.

However, the composition (B) is preferably used at an acid pH.

The compositions (A) and (B) can be packaged in the forms customarily used, especially in dyeing hair, in particular in the form of a lotion, thickened to a greater or lesser extent, a gel or an emulsion, any or all of which may be packaged as an aerosol.

The appropriate medium for dyeing is generally an aqueous medium which can consist of water or of a mixture of water and a solvent which, when the composition is applied to the hair, must be cosmetically acceptable.

Such solvents are chosen more particularly from the organic solvents such as the $C_1$-$C_6$-lower alcohols, such as ethyl alcohol, propyl or rsopropyl alcohol or tertiary butyl alcohol, ethylene glycol, propylene glycol, the monomethyl, monoethyl or monobutyl ethers of ethylene glycol, ethylene glycol monoethyl ether-acetate, the monomethyl ethers of propylene glycol and of dipropylene glycol and methyl lactate.

The solvents particularly preferred are ethyl alcohol and propylene glycol.

When they are used, the solvents are most particularly in concentrations of between 10 and 50% for the lower alcohols and for high concentrations of mono- or di-hydroxyindole.

The compositions (A) and (B) according to the invention can also be stored in an anhydrous solvent medium. The solvents are chosen from the solvents defined above. The medium containing less than 1% of water is termed an anhydrous medium.

The compositions according to the invention, when they are used for dyeing hair, can also contain all other adjuvants customarily used in cosmetics and more particularly anionic, cationic, non-ionic or amphoteric surfactants or mixtures thereof, thickeners, fragrances, sequestering agents, film-forming agents, treatment agents, dispersing agents, conditioners, preservatives, opacifying agents and swelling agents for the keratinous fibers.

The compositions (A) and/or (B) which can be used in the process according to the invention can contain other dyes customarily used for dyeing keratinous fibers and in particular direct dyes, such as the nitrated derivatives of benzene, oxidation dyes of the para or ortho type and couplers or so-called "rapid" oxidation dyes, that is to say molecules having a benzene-containing structure, precursors of dyes capable of generating colored compounds by simple oxidation in the air during the exposure time on the hair, which is generally less than 1 hour, and in the absence of any other oxidizing agent.

These compositions can also contain quinone dyes from the family of the benzoquinones, the imines or diimines of benzoquinones, the naphthoquinones, naphthoquinone imines or naphthoquinone diimines, which do not comply with the potential conditions defined above. These dyes are, in this case, used to supply their inherent hue to the dye.

With a view to the implementation of the process according to the invention, it is possible to package the various compositions in a multi-compartment device also called a dyeing kit or necessary containing all the components intended to be applied for a given dyeing on the keratinous fibers and in particular hair, in successive applications with or without premixing.

Devices of this type can more particularly comprise a first compartment containing the composition (A) and a second compartment containing the composition (B). Another variant can also consist in storing the composition (A) or the composition (B) in an anhydrous solvent medium and in providing a third compartment containing an aqueous medium which is appropriate for the dyeing and cosmetically acceptable if the compositions are intended to be applied to hair. In this case, the contents of the third compartment are mixed just before use in one or other of the two compartments containing the anhydrous compositions (A) and (B).

The process according to the invention is preferably carried out by applying the composition (A) in a first period and then the composition (B) in a second period. It can be used, in particular, for dyeing human hair, which may be in the natural state or already dyed and may or may not have been given a permanent-wave or have been straightened, and hair which has been severely or slightly bleached and may have been given a permanent-wave.

In this case, the composition (A) is applied at a temperature which can be tolerated by the head, that is to say of between 25° and 40° C., for 2 to 30 minutes, and this application is followed, with or without intermediate rinsing, by the application of the composition (B) containing the quinone derivative which is kept in contact with the hair for 5 to 30 minutes, the dyeing temperature likewise being between 25° and 40° C.

The process according to the invention can also be carried out, with a view to changing the hue or reviving a dyeing which had been carried out using mono-or di-hydroxyindole, by applying the composition (B) several hours or days after the dyeing using mono- or dihydroxyindoles.

It is also possible to use this process for dyeing furs and wool under the customary industrial conditions with respect to temperature, contact time and concentration.

The novel compounds of formula (IV) which can be used according to the invention can be prepared by the following processes:

A/ When (A) denotes the $CH_2SR$ group and $R_{21}$ denotes hydrogen (formula IV(A)). These compounds IV(A) are prepared from the corresponding para-aminophenols by oxidation with ferric chloride or ferric sulphate, in accordance with the following reaction scheme I.

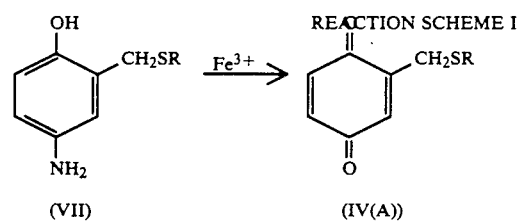

The compounds of formula (VII) are prepared in two steps from the substituted nitrophenol of formula (IX), in which Y denotes a halogen atom, in accordance with the reaction scheme given below:

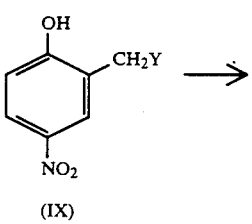

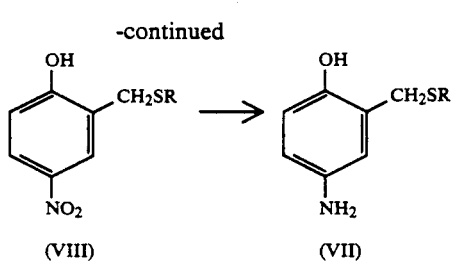

(VIII)   →   (VII)

The compound of formula (VII) is obtained by reduction of the compound of formula (VIII), where R has the meanings defined above. Amongst the conventional reduction methods, the following may be cited: reduction by sodium hydrosulphite in an alkaline medium at a temperature below 80° C., or a catalytic reduction in an aqueous-alcoholic medium, under hydrogen pressure, in the presence of a catalyst such as palladium-on-charcoal or nickel.

The compound of formula (VIII) can be prepared by the action of a thiolate of formula:

M—S—R in which M represents an alkali metal or alkaline earth metal and R has the meanings defined above, on the compound of formula (IX).

The thiolate can advantageously be prepared in situ in accordance with the reaction scheme:

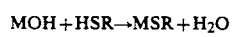

MOH + HSR → MSR + H$_2$O the compound HSR also being able to serve as a solvent.

Amongst the solvents which can be used for the preparation of compounds of formula (VIII), the following may be cited, in addition to the compound HSR: dioxane, N,N-dimethylformamide and N-methylpyrrolidone, used on their own or as a mixture. In general, the reaction temperature is below 100° C.

B/ When (A) denotes the SR group, R having the meanings indicated above and R$_{21}$ being hydrogen or alkyl (for the compounds of formula (IV) (compound IV(B)).

These compounds IV(B) are prepared from benzoquinone compounds of formula (X) by reacting two moles of the quinone derivative with one mole of thiol (RSH), in an alcohol/water solvent or in ethanol, in accordance with the reaction scheme II.

REACTION SCHEME II

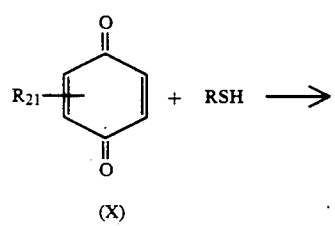

(X)   + RSH   →

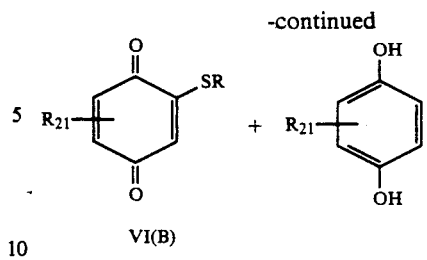

VI(B)

C/ When (A) and R$_{21}$ simultaneously denote SR, R having the meaning indicated for the compounds (IV) (compound IV(C)).

These compounds are prepared by reacting 4 moles of p-benzoquinone with 3 moles of derivative of formula RSH in ethanol/water or absolute ethanol, in accordance with the reaction scheme III.

REACTION SCHEME III

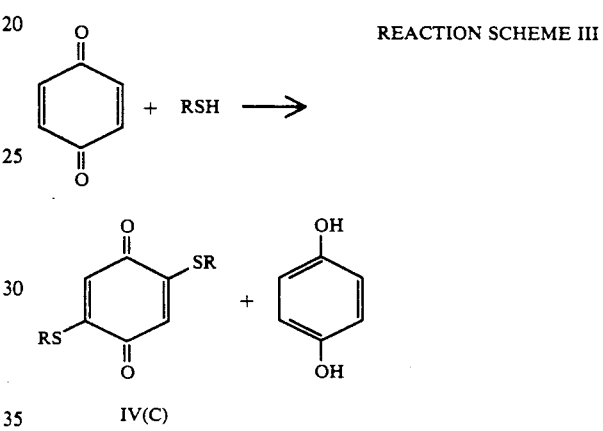

IV(C)

The following examples are intended to illustrate the preparation of the compounds of formula (IV).

PREPARATION EXAMPLE 1

Preparation of 2-(methylthio)methyl-1,4-benzoquinone Formula IV(A): R=CH$_3$:

1st step

Preparation of 4'-amino-2-[(methylthio)methyl]phenol

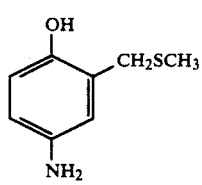

0.085 mole (17g) of 4-nitro-2-[(methylthio)-methyl]-phenol is added to a solution of 16 g of sodium hydroxide (NaOH) in pellets in 135 ml of water and 55 g of sodium hydrosulphite are then added in portions so as to keep the temperature between 70° and 75° C. Stirring is continued for 30 minutes at 75° C. after the end of the addition. The expected product is obtained, by neutralization of the reaction mixture with acetic acid, after cooling. After centrifuging, then washing with water and drying, it is recrystallized from 96° ethanol. It melts at 166° C.

The analysis of the product obtained gives the following results:

| Analysis for $C_8H_{11}NOS$ | | | | |
| --- | --- | --- | --- | --- |
| | C | H | N | O | S |
| Calculated | 56.79 | 6.55 | 8.28 | 9.45 | 18.91 |
| Found | 56.69 | 6.49 | 8.25 | 9.56 | 18.76 |

2nd step

4-Amino-[(methylthio)methyl]phenol (8.45 g, 0.05 mole) is dissolved in a mixture of ethyl acetate (200 ml), water (200 ml) and concentrated hydrochloric acid (6 ml). A solution of ferric chloride (16.25 g in 125 ml of water, 0.1 mole) is added thereto. At the end of a quarter of an hour, the violet-black solution is extracted 4 times with ethyl acetate. The organic phases are dried over sodium sulphate and concentrated to one quarter of the volume. The organic phase is treated with vegetable black and filtered and the solvent is evaporated. An orange-brown oil is obtained which crystallizes from diisopropyl ether. An orange powder is obtained:
Weight: 3 g.
Yield: 36%.
m.p.: 43° C.

| Analysis for $C_8H_8O_2S$ | | | |
| --- | --- | --- | --- |
| | C | H | O | S |
| Calculated | 57.12 | 4.79 | 19.02 | 19.06 |
| Found | 57.23 | 4.78 | 19.20 | 19.16 |

PREPARATION EXAMPLE 2

Preparation of 2-($\beta$-hydroxyethylthio)methyl-1,4-benzoquinone
(Formula IV(A): $R=CH_2CH_2OH$)

1st step

Preparation of 4-amino-2-[($\beta$-hydroxyethylthio)methyl]-phenol

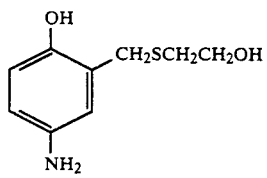

0.085 mole (19.5 g) of 4-nitro-2-[($\beta$-hydroxyethylthio)methyl]phenol is added to a solution of 16 g of sodium hydroxide (NaOH) in pellets in 135 ml of water and 55 g of sodium hydrosulphite are then added in portions so as to keep the temperature between 70° C. and 75° C. Stirring is continued for 20 minutes at 75° C. after the end of the addition. The expected product is precipitated, by neutralization of the reaction mixture with acetic acid, after cooling. After centrifuging, then washing with water and drying, the product obtained is recrystallized from acetonitrile. It melts at 121° C.

The analysis of the product obtained gives the following results:

| Analysis for $C_9H_{13}NO_2S$ | | | | |
| --- | --- | --- | --- | --- |
| | C | H | N | O | S |
| Calculated | 54.24 | 6.58 | 7.03 | 16.06 | 16.09 |
| Found | 54.02 | 6.62 | 7.00 | 16.17 | 15.92 |

2nd step

A solution of ferric chloride (0.65 g in 50 ml of water) is added to a solution of 4-amino-2-[($\beta$-hydroxyethylthio)methyl]phenol (0.4 g, 2 mmoles). The mixture is extracted immediately with dichloromethane and the organic phase is dried and concentrated. The brown oil obtained crystallizes. After recrystallization in a mixture of diisopropyl ether/hexane, orange crystals are obtained:
Weight: 0.2 g.
Yield 50%.
m.p.: 57° C.

| Analysis for $C_9H_{10}O_3S$ | | | |
| --- | --- | --- | --- |
| | C | H | O | S |
| Calculated | 54.53 | 5.08 | 24.21 | 16.17 |
| Found | 54.31 | 5.07 | 23.94 | 16.56 |

PREPARATION EXAMPLE 3

Preparation of 2-($\beta$-hydroxyethylthio)-1,4-benzoquinone (Formula IV(B): $R=CH_2CH_2OH$, $R_{21}=H$)

2-Mercaptoethanol (25.9 ml, 0.368 mole) is added in a single amount to a suspension of p-benzoquinone (80 g, 0.736 mole) in absolute ethanol (500 ml), with stirring and while bubbling nitrogen through the suspension. The temperature rises from 22° C. to 45° C. within 30 seconds and the mixture becomes a homogeneous red-brown. At the end of 15 minutes, a precipitate appears. The mixture is left to stand with stirring for 2 hours and filtered through a no. 4 frit. The orange-red precipitate is washed with 3×50 ml of cold ethanol and dried. Orange crystals are obtained
Weight: 53 g.
Yield: 78%.
m.p.: 108-109° C.

| Analysis for $C_8H_8O_3S$ | | | |
| --- | --- | --- | --- |
| | C | H | O | S |
| Calculated | 52.16 | 4.38 | 26.06 | 17.41 |
| Found | 52.03 | 4.34 | 26.28 | 17.25 |

PREPARATION EXAMPLE 4

Preparation of 2-hydroxyethylthio-6-methyl-1,4-benzoquinone (Formula IV(B): $R=CH_2CH_2OH$, $R_{21}=6-CH_3$)

Methyl-p-benzoquinone 12.2 g, 0.1 mole) and 2-mercaptoethanol (3.9 g, 0.05 mole) are mixed in absolute ethanol (70 ml) under nitrogen and with stirring. The temperature rises to 50° C. The mixture is cooled in a bath of ice-water and left to stand, with stirring, for 2 hours at ambient temperature. The solution is concentrated under vacuum and the oil obtained is chromatographed on Silica 60 (eluent: dichloromethane). According to $^1H$ and $^{13}C$ NMR, a first fraction (3 g) is a 50/50 mixture of two products: 2-hydroxyethylthio-5-methyl-1,4-benzoquinone and 2-hydroxyethylthio-6-methyl-1,4-benzoquinone. A second fraction gives the expected product:
Orange powder.
Weight: 0.5 g.
m.p 82° C.

| Analysis for $C_9H_{10}O_3S$ | | | | |
|---|---|---|---|---|
| | C | H | O | S |
| Calculated | 54.53 | 5.08 | 24.21 | 16.17 |
| Found | 54.33 | 4.94 | 24.38 | 16.05 |

PREPARATION EXAMPLE 5

Preparation of 2,5-bis-(β-hydroxyethylthio)-1,4benzoquinone (Formula IV(C): R=CH$_2$CH$_2$OH)

2-Mercaptoethanol (3.5 ml, 0.05 mole) is added in a single amount to an ethanolic solution of p-benzoquinone (10.81 g, 0.1 mole) and the mixture is allowed to stand, with stirring, for ½ hour. Further 2-mercaptoethanol (1.75 ml, 0.025 mole) is added and the mixture is allowed to stand, with stirring, for 2 hours. The mixture is filtered and the precipitate is washed with absolute ethanol. Dark red crystals of the expected derivative are obtained:

Weight: 6.7 g.
Yield: 34%.
m.p.: 120–122° C.

| Analysis for $C_{10}H_{12}O_4S_2$ | | | | |
|---|---|---|---|---|
| | C | H | O | S |
| Calculated | 46.14 | 4.65 | 24.58 | 24.63 |
| Found | 46.11 | 4.69 | 24.68 | 24.29 |

The following examples are intended to illustrate the dyeing process according to the invention, without having a limiting character.

EXAMPLE 1

A lock of 1 g of natural hair containing 90% white hair is impregnated with 5 ml of a 2.5% solution of 5,6-dihydroxyindole in a 90/10 aqueous-ethanolic medium for 15 minutes. The lock is rinsed under running water and towel-dried. This lock is re-impregnated with 5 ml of a 2% solution of 1,4-benzoquinone in a 50/50 aqueous-ethanolic medium for 8 minutes. The lock is rinsed under running water and shampooed with a 5% aqueous solution of sodium lauryl sulphate. A lock with a deep black color with slight bluish glints is obtained.

The oxidation-reduction potential of 5,6-dihydroxyindole, determined in a phosphate medium at pH 7 on a vitreous carbon electrode by voltametry, is $E_i$=90 mV.

The oxidation-reduction potential of 1,4-benzoquinone, determined in a phosphate medium at pH 7 by polarography on a mercury electrode relative to a calomel electrode, is $E_q$=10 mV. $\Delta E$=80 mV.

EXAMPLE 2

In a first period, a lock of 1 g of natural grey hair (90% white hair) is impregnated with 5 ml of a 2.5% solution of 4-hydroxy-5-methoxyindole in a 50/50 aqueous-ethanolic solution for 15 minutes at ambient temperature. The lock is rinsed under running water and towel-dried. In a second period, the same lock is impregnated with 5 ml of a 2% solution of 1,4-benzoquinone in a 50/50 aqueous-ethanolic medium for 8 minutes. The lock is washed under running water and finally shampooed with 5% sodium lauryl sulphate. A deeply colored lock with a violet hue is obtained.

The values of the oxidation-reduction potentials determined as in Example 1 are:

$E_i$=110 mV $E_q$=10 mV $\Delta E$=100 mV

EXAMPLE 3

A lock of 1 g of natural grey hair (containing 90% white hair) is taken and impregnated for 15 minutes with a 2.5% 60/40 aqueous-ethanolic solution of 2-methyl-5,6-dihydroxyindole. The lock is washed under running water and then towel-dried. 5 ml of a 2% solution of 1,4-benzoquinone in a 50/50 aqueous-alcoholic medium are then applied for 9 minutes The lock is washed under running water and then shampooed with 5% sodium lauryl sulphate. A raven-colored lock is obtained.

The values of the oxidation-reduction potentials, determined as in Example 1, are as follows:

$E_i$=45 mV $E_q$=10 mV $\Delta E$=35 mV

EXAMPLE 4

A 2.5% solution of 6-hydroxy-7-methoxyindole in an 80/20 aqueous-alcoholic medium is prepared 5 ml of this solution are applied to a lock of 1 g of natural hair (grey with 90% white hair) for 15 minutes. The lock is rinsed under running water and then towel-dried. This lock is re-impregnated for 10 minutes with 5 ml of a 2% 50/50 aqueous-alcoholic solution of 1,4-benzoquinone. The lock is rinsed with water and finally shampooed with 5% sodium lauryl sulphate A chestnut-colored lock is obtained.

The values of the oxidation-reduction potentials, determined as in Example 1, are as follows:

$E_i$ 60 mV $E_q$=10 mV $\Delta E$=150 mV

EXAMPLE 5

A 2.5% solution of 5-methoxy-6-hydroxyindole in a 70/30 aqueous-alcoholic solution is prepared. This solution is left on a lock of grey hair containing 90% white hair for 15 minutes at ambient temperature. The lock is rinsed and towel-dried and the coloring is then developed using a 2% 50/50 aqueous-alcoholic solution of 1,4-benzoquinone. This solution is left on the hair for 8 minutes and after rinsing, shampooing, rinsing and drying a black color is obtained.

The values of the oxidation-reduction potentials, determined as in Example 1, are:

$E_i$=180 mV $E_q$=10 mV $\Delta E$=170 mV

EXAMPLE 6

A lock of natural grey hair containing 90% white hair is pretreated for 15 minutes with a 60/40 aqueous-alcoholic solution containing 2.5% of 5-hydroxy-6-methoxyindole. This solution is left on the hair for 15 minutes and after rinsing ad towel-drying the coloring is developed using a 2% 50/50 aqueous-alcoholic solution of 1,4-benzoquinone. This solution is left on the hair for 8 minutes and after rinsing, shampooing, rinsing again and drying, a light chestnut color is obtained.

The values of the oxidation-reduction potentials, determined as in Example 1, are:

$E_i$=230 mV $E_q$=10 mV $\Delta E$=220 mV

EXAMPLE 7

A 2.5% 80/20 aqueous-alcoholic solution of 7-hydroxyindole is applied to a lock of natural grey hair containing 90% white hair. The solution is left on the hair for 15 minutes, the lock is rinsed and towel-dried and a 50/50 aqueous-alcoholic solution containing 2% of 1,4-benzoquinone is applied. This solution is left on the hair for 15 minutes, the lock is washed, towel-dried and dried and a very intense deep violet color is obtained.

The values of the oxidation-reduction potentials, determined as in Example 1, are:

$E_i = 285$ mV  $E_q = 10$ mV  $\Delta E = 275$ mV

EXAMPLE 8

A lock of grey hair is treated with an 80/20 aqueous-alcoholic solution containing 2.5% of 6-hydroxyindole. After the solution has remained on the hair for 15 minutes, the lock is rinsed and towel-dried and a composition based on 50/50 water/alcohol and 2% of 1,4-benzoquinone is applied. This composition is left on the hair for 9 minutes, after which the lock is washed with a shampoo, rinsed and dried and a golden chestnut color is obtained.

The values of the oxidation-reduction potentials, determined as in Example 1, are:

$E_i = 320$ mV  $E_q = 10$ mV  $\Delta E = 310$ mV

EXAMPLE 9

A lock of natural grey hair containing 90% white hair is treated with a 1% 60/40 aqueous-alcoholic solution of (5 or 6)-acetoxy-(6 or 5)-hydroxyindole. This solution is left on the hair for 15 minutes, after which the lock is rinsed and towel-dried and a 2% 50/50 aqueous-alcoholic solution of 1,4-benzoquinone is applied. This solution is left on the hair for 8 minutes, the lock is then washed, rinsed and towel-dried and a golden chestnut color is obtained.

The values of the oxidation-reduction potentials, determined as in Example 1, are:

$E_i = 110$ mV or 270 mV  $E_q = 10$ mV  $\Delta E = 100$ mV or 260 mV

EXAMPLE 10

After having pretreated a lock of grey hair containing 90% white hair for 15 minutes with a 2.5% 60/40 aqueous-alcoholic solution of 2,3-dimethyl-5,6-dihydroxyindole, the lock is rinsed and towel-dried and a 2% 50/50 aqueous-alcoholic solution of 1,4-benzoquinone is applied for 8 minutes. The procedure is as above and a mahogany color is obtained.

The values of the oxidation-reduction potentials, determined as in Example 1, are:

$E_i = 30$ mV  $E_q = 10$ mV  $\Delta E = 20$ mV

EXAMPLE 11

The application process is identical to that of Example 10, but the indole dye this time is 4-hydroxy-5-ethoxyindole. A deep violet color is obtained.

The values of the oxidation-reduction potentials, determined as in Example 1, are:

$E_i = 110$ mV  $E_q = 10$ mV  $\Delta E = 100$ mV

EXAMPLE 12

Following the procedure of Example 10, with 1-methyl-5,6-dihydroxyindole, a deep raven coloration is obtained.

The values of the oxidation-reduction potentials, determined as in Example 1, are:

$E_i = 105$ mV  $E_q = 10$ mV  $\Delta E = 95$ mV

EXAMPLE 13

Starting from a 2% 50/50 aqueous-alcoholic solution of 2,3-dimethyl-4-hydroxy-7-methoxy indole and using the same developing composition as in Example 10 and following the same mode of operation, a mahogany color is obtained.

The values of the oxidation-reduction potentials, determined as in Example 1, are:

$E_i = 20$ mV  $E_q = 10$ mV  $\Delta E = 10$ mV

EXAMPLE 14

The process is the same as that described in Example 10 and the compositions are identical except that the dye used is 2-methyl-5,6-dihydroxyindole. After developing, a very deep chestnut color is thus obtained.

The values of the oxidation-reduction potentials, determined as in Example 1, are:

$E_i = 45$ mV  $E_q = 10$ mV  $\Delta E = 35$ mV

EXAMPLE 15

A lock of naturally grey hair is treated with an 80/20 aqueous-alcoholic solution containing 2.5% of 5,6-dihydroxyindole. After the solution has remained on the hair for 15 minutes and the lock has been rinsed and towel-dried, the color is developed with 2-methyl-1,4- benzoquinone (toluquinone) dissolved in a concentration of 2% in a 50/50 aqueous-alcoholic solution. After having rinsed, washed, rinsed again and dried, a deep black color with bluish glints is obtained.

The values of the oxidation-reduction potentials, determined as in Example 1, are:

$E_i = 90$ mV  $E_q = 45$ mV  $\Delta E = 135$ mV

EXAMPLE 16

Following the same procedure as in Example 15 and replacing the toluquinone by 2,6-dimethyl-1,4-benzoquinone, a mid-chestnut color with purplish glints is obtained.

The values of the oxidation-reduction potentials, determined as in Example 1, are:

$E_i = 90$ mV  $E_q = -70$ mV  $\Delta E = 160$ mV

EXAMPLE 17

If, in Example 16, the toluquinone is replaced by the same amount of 2-methoxy-1,4-benzoquinone, a deep black color is obtained.

The values of the oxidation-reduction potentials, determined as in Example 1, are:

$E_i=90$ mV  $E_q=40$ mV  $\Delta E=130$ mV

EXAMPLE 18

A lock of natural grey hair containing 90% white hair is treated with a 50/50 aqueous-ethanolic solution containing 2.5% of 5,6-dihydroxyindole. After this solution has remained on the hair for 15 minutes, the lock is rinsed and towel-dried and a 50/50 aqueous-ethanolic composition containing 2% of 1,2-tetrachlorobenzoquinone is applied. This composition is left on the hair for 10 minutes and the lock is rinsed, shampooed, rinsed again and dried. A deep grey color is obtained.

$E_i=90$ mV  $E_q=-80$ mV  $\Delta E=170$ mV

EXAMPLE 19

The pretreatment composition is the same as in Example 16 and the developing composition is based on 2,6-dimethyl-5-acetylamino-1,4-benzoquinone. A light chestnut-grey color is obtained.

The values of the oxidation-reduction potentials, determined as in Example 1, are:

$E_i=90$ mV  $E_q=-65$ mV  $\Delta E=155$ mV

EXAMPLE 20

The pretreatment is the same as in Example 16. It is followed by a development with a 50/50 aqueous-alcoholic solution containing 2% of 1,4-naphthoquinone. This solution is left on the hair for 8 minutes and the lock is rinsed, washed, rinsed again and dried. A light chestnut color is observed.

The values of the oxidation-reduction potentials, determined as in Example 1, are:

$E_i=90$ mV  $E_q=-185$ mV  $\Delta E=275$ mV

EXAMPLE 21

The procedure is as in Example 16, the development being carried out with the aid of N-2,6-trichloro-1,4-benzoquinone imine. The color obtained is deep chestnut.

The values of the oxidation-reduction potentials, determined as in Example 1, are:

$E_i=90$ mV  $E_q=-90$ mV  $\Delta E\geqq180$ mV

EXAMPLE 22

First of all a pretreatment is carried out using a 50/50 aqueous-alcoholic solution containing 2% of 1,4-benzoquinone. After this solution has remained on the hair for 15 minutes, the hair is rinsed and towel-dried and the color is developed using an 80/20 aqueous-alcoholic solution containing 2.5% of 5,6-dihydroxyindole at pH 3. This solution is left on the hair for 15 minutes and the hair is rinsed, shampooed, rinsed again and dried. A golden chestnut color is obtained on hair which was initially grey with 90% white hair.

The values of the oxidation-reduction potentials, determined as in Example 1, are:

$E_i=90$ mV  $E_q=10$ mV  $\Delta E=80$ mV

EXAMPLE 23

| Composition (A) | |
|---|---|
| 5,6-Dihydroxyindole | 2.5 g |
| Ethyl alcohol | 10.0 g |
| Hydroxypropylguar sold under the name JAGUAR HP 60 by the MEYHALL company | 1.0 g |
| Glycoside alkyl ether sold in a concentration of 60% AS under the name TRITON CG 110 by the SEPPIC company | 5.0 g |
| Preservatives | 0.15 g |
| Spontaneous pH = 6.7 | |
| Water | qs 100.0 g |
| Composition (B) | |
| 1,2-Naphthoquinone | 0.4 g |
| Propylene glycol monomethyl ether | 20.0 g |
| Sodium lauryl ether-sulphate with 2 moles of ethylene oxide sold under the name SACTIPON 8533 by the LEVER company | 6.0 g AS |
| Nonylphenol with 9 moles of ethylene oxide sold under the name SINNOPAL NP 9 by the HENKEL company | 3.0 g |
| Spontaneous pH = 3.7 | |
| Water | qs 100.0 g |

Grey hair containing 90% white hair is treated for 15 minutes with composition (A).

After rinsing, composition (B) is applied for 10 minutes.

The hair is rinsed again and dried. Hair dyed deep grey with blue glints is then obtained.

The values of the oxidation-reduction potentials, determined as in Example 1, are:

$E_i=90$ mV  $E_q=-55$ mV  $\Delta E=145$ mV

EXAMPLE 24

Composition (A) is identical to that of Example 23.

| Composition (B1) | |
|---|---|
| 1,2-Naphthoquinone | 0.05 g |
| Ethylene glycol monobutyl ether | 30.0 g |
| Spontaneous pH = 3.5 | |
| Water | qs 100.0 g |

Composition (A) is applied to grey hair containing 90% white hair for 15 minutes.

The hair is rinsed and composition (B1) is then applied for 10 minutes.

After rinsing and drying, the hair is colored a mid-intensity blue hue.

The values of the oxidation-reduction potentials, determined as in Example 1, are:

$E_i=90$ mV  $E_q=-55$ mV  $\Delta E=145$ mV

EXAMPLE 25

Composition (A) is identical to that of Example 23.

| Composition (B2) | |
|---|---|
| Potassium salt of 1,2-naphthoquinone-4-sulphonic acid | 0.9 g |
| Ethyl alcohol | 10.0 g |
| Spontaneous pH = 3.4 | |
| Water | qs 100.0 g |

Composition (A) is applied to grey hair containing 90% white hair for 15 minutes.

After rinsing, the hair is treated with composition (B2) for 10 minutes.

The hair is rinsed again and dried.

Hair dyed a very deep natural grey is then obtained.

The values of the oxidation-reduction potentials, determined as in Example 1, are:

$E_i = 90$ mV  $E_q = -20$ mV  $\Delta E = 110$ mV

EXAMPLE 26

The pretreatment composition and method are the same as in Example 16. They are followed by a development with a 2% 50/50 aqueous-alcoholic solution of 2-chloro-1,4-benzoquinone for 10 minutes. The hair is rinsed, washed and dried.

The color obtained is deep black.

The values of the oxidation-reduction potentials, determined as in Example 1, are:

$E_i = 90$ mV  $E_q = 20$ mV  $\Delta E = 70$ mV

EXAMPLE 27

Following the same procedure as in Example 15, but replacing the toluquinone by 2-($\beta$-hydroxyethylthio)-1,4-benzoquinone, a black coloration is obtained.

The values of the oxidation-reduction potentials, determined as in Example 1, are:

$E_i = 90$ mV  $E_q = 25$ mV  $\Delta E = 65$ mV

EXAMPLE 28

Following the same procedure as in Example 15, but replacing the toluquinone by 2,5-bis-($\beta$-hydroxyethylthio)-1,4-benzoquinone, a deep chestnut shade is obtained.

The values of the oxidation-reduction potentials, determined as in Example 1, are:

$E_i = 90$ mV  $E_q = 30$ mV  $\Delta E = 60$ mV

EXAMPLE 29

Following the same procedure as in Example 15, but replacing the toluquinone by 2-($\beta$-carboxyethylthio)-1,4-benzoquinone, a deep chestnut shade is obtained.

The values of the oxidation-reduction potentials, determined as in Example 1, are:

$E_i = 90$ mV  $E_q = 40$ mV  $\Delta E = 50$ mV

EXAMPLE 30

Following the same procedure as in Example 15, but replacing the toluquinone by 2-methylthiomethyl-1,4-benzoquinone, a black coloration is obtained.

The values of the oxidation-reduction potentials, determined as in Example 1, are:

$E_i = 90$ mV  $E_q = 45$ mV  $\Delta E = 45$ mV

EXAMPLE 31

Following the same procedure as in Example 15, but replacing the toluquinone by 2-($\beta$-hydroxyethylthiomethyl)-1,4-benzoquinone, a deep chestnut coloration is obtained.

The values of the oxidation-reduction potentials, determined as in Example 1, are:

$E_i = 90$ mV  $E_q = 55$ mV  $\Delta E = 35$ mV

EXAMPLE 32

Following the same procedure as in Example 15, but replacing the toluquinone by 2-($\beta$-carboxyethoxy)-1,4-benzoquinone, a deep chestnut coloration is obtained.

The values of the oxidation-reduction potentials, determined as in Example 1, are:

$E_i = 90$ mV  $E_q = 15$ mV  $\Delta E = 105$ mV

EXAMPLE 33

A lock of grey hair containing 90% white hair is treated with a 2.5% 90/10 aqueous-alcoholic solution of 2,3-dimethyl-5-hydroxy-6-aminoindole. This solution is left in contact with the hair for 15 minutes, the lock is rinsed and towel-dried and a 50/50 aqueous-alcoholic solution containing 2% of 1,2-naphthoquinone is applied. The contact time is 15 minutes, the lock is washed, towel-dried and dried and a deep grey shade is obtained.

The values of the oxidation-reduction potentials, determined as in Example 1, are:

$E_i = 45$ mV  $E_q = 55$ mV  $\Delta E = 100$ mV

EXAMPLE 34

A lock of grey hair containing 90% white hair is treated with a 2.5% 90/10 aqueous-alcoholic solution of 2,3-dimethyl-5-amino-6-hydroxyindole. This solution is left in contact with the hair for 15 minutes, the lock is rinsed and towel-dried and a 50/50 aqueous-alcoholic solution containing 2% of 1,4-benzoquinone is applied. The contact time is 15 minutes, the lock is washed, towel-dried and dried and a mid-chestnut coloration is obtained.

The values of the oxidation-reduction potentials, determined as in Example 1, are:

$E_i = 10$ mV  $E_q = 10$ mV  $\Delta E = 0$

EXAMPLE 35

Following the same procedure as in Example 2, but replacing the 1,4-benzoquinone by 2-($\beta$-hydroxyethylthio)-6-methyl-1,4-benzoquinone, a violet coloration is obtained.

The values of the oxidation-reduction potentials, determined as in Example 1, are:

$E_i = 110$ mV  $E_q = -50$ mV  $\Delta E = 160$ mV

EXAMPLE 36

Following the same procedure as in Example 2, but replacing the 1,4-benzoquinone by 2-methoxymethyl-1,4-benzoquinone, a deep violet-colored lock is obtained.

The values of the oxidation-reduction potentials, determined as in Example 1, are:

$E_i = 110$ mV  $E_q = 25$ mV  $\Delta E = 85$ mV

EXAMPLE 37

Following the same procedure as in Example 5, but replacing the 1,4-benzoquinone by 2-($\beta,\gamma$-dihydroxypropylthio)-1,4-benzoquinone, a deep grey coloration is obtained.

The values of the oxidation-reduction potentials, determined as in Example 1, are:

$E_i = 180$ mV  $E_q = 30$ mV  $\Delta E = 150$ mV

EXAMPLE 38

Following the same procedure as in Example 15, but replacing the toluquinone by 2-($\beta$-hydroxyethoxy)-1,4-benzoquinone, a deep chestnut coloration is obtained.

The values of the oxidation-reduction potentials, determined as in Example 1, are:

$E_i = 90$ mV  $E_q = -50$ mV  $\Delta E = 140$ mV

EXAMPLE 39

Following the same procedure as in Example 15, but replacing the toluquinone by N-methylsulphonyl-1,4-benzoquinone monoimine, a deep chestnut coloration is obtained.

The values of the oxidation-reduction potentials, determined as in Example 1, are:

$E_i = 90$ mV  $E_q = 65$ mV  $\Delta E = 25$ mV

EXAMPLE 40

Following the same procedure as in Example 15, but replacing the toluquinone by N-phenylsulphonyl-1,4-benzoquinone monoimine, a mid-chestnut coloration is obtained.

The values of the oxidation-reduction potentials, determined as in Example 1, are:

$E_i = 90$ mV  $E_q = 60$ mV  $\Delta E = 30$ mV

We claim:

1. A process for dyeing kratinous fibers comprising applying to said fibers at least one composition A comprising in a cosmetically acceptable medium at least one monohydroxyindole or dihydroxyindole, the application of said composition A to said fibers being preceded or followed by the application to said fibers of composition B comprising in a cosmetically acceptable medium at least one quinone derivative selected from the group consisting of orthobenzoquinone, parabenzoquinone, orthobenzoquinone monoimine, orthobenzoquinone diimine, parabenzoquinone monoimine, parabenzoquinone diimine, 1,2-naphthoquinone, 1,4-naphthoquinone, orthobenzoquinone sulphonamide, parabenzoquinone sulphonamide, $\alpha,\omega$-alkylene-bis-1,4-benzoquinone, 1,2-naphthoquinone monoimine, 1,2-naphthoquinone diimine, 1,4-naphthoquinone monoimine, and 1,4-naphthoquinone diimine;

the said monohydroxyindole or dihydroxyindole and said quinone derivative being chosen such that the oxidation-reduction potential difference, $\Delta E$, between the oxidation-reduction potential $E_i$ of said monohydroxyindole or dihydroxyindole, determined at pH 7 in a phosphate medium on a vitreous carbon electrode by voltametry, and the oxidation-reduction potential $E_q$ of said quinone derivative, determined at pH 7 in a phosphate medium by polarography on a mercury electrode and relative to a saturated calomel electrode, is such that $\Delta E = E_i - E_q \leq 320$ mV.

2. The process of claim 1 wherein said monohydroxyindole or dihydroxyindole has the formula

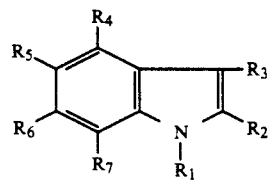

(I)

wherein $R_1$ represents hydrogen or $C_1$-$C_4$ alkyl, $R_2$ and $R_3$, each independently, represent hydrogen, $C_1$-$C_4$ alkyl, carboxyl, $C_1$-$C_4$ alkoxycarbonyl, $C_1$-$C_4$ hydroxyalkyl or $C_1$-$C_4$ aminoalkyl, and $R_4$, $R_5$, $R_6$ and $R_7$, each independently represent hydrogen; $C_1$-$C_4$ alkyl; amino; amino substituted by one or two $C_1$-$C_4$ alkyl groups; amino substituted by one or two $C_1$-$C_4$ hydroxyalkyl groups; $C_2$-$C_6$ acylamino; carboxyl; $C_1$-$C_4$ carboxyalkyl; $C_1$-$C_4$ alkoxycarbonyl;

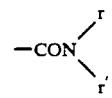

wherein r and R', each independently, represent hydrogen or $C_1$-$C_4$ alkyl; halogen; $C_1$-$C_4$ hydroxyalkyl; $C_1$-$C_4$ aminoalkyl; OH; and OZ wherein Z represents linear or branched $C_1$-$C_{20}$ alkyl, aralkyl, formyl, linear or branched $C_2$-$C_{20}$ acyl, linear or branched $C_3$-$C_{20}$ alkenyl, $-SiR_{11}R_{12}R_{13}$, $-P(O)(OR_8)_2$ or $R_8OSO_2-$, or the pairs $R_4$ and $R_5$, or $R_5$ and $R_6$, or $R_6$ and $R_7$, form, together with the carbon atoms to which each pair is attached, a ring containing a carbonyl group, a thiocarbonyl group, a

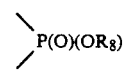

group or a

group, with the proviso that at least one of $R_4$, $R_5$, $R_6$ and $R_7$ represents an OH group, $R_8$ and $R_9$ represent hydrogen or $C_1$-$C_4$ alkyl, $R_{10}$ represents $C_1$-$C_4$ alkoxy, $C_1$-$C_4$ monalkylamino or $C_1$-$C_4$ dialkylamino, and $R_{11}$, $R_{12}$ and $R_{13}$, each independently, represent linear or branched alkyl, and the alkali metal, alkaline earth metal, ammonium and amine salts of said monohydroxyindole or dihydroxyindole.

3. The process of claim 1 wherein said monohydroxyindole or dihydroxyindole is selected from the group consisting of 4-hydroxyindole
4-hydroxy-5-methoxyindole
4-hydroxy-5-ethoxyindole
5-hydroxyindole
2-carboxy-5-hydroxyindole
5-hydroxy-6-methoxyindole
6-hydroxyindole
6-hydroxy-7-methoxyindole
5-methoxy-6-hydroxyindole
2-carboxy-6-hydroxyindole
2-ethoxycarbonyl-6-hydroxyindole
7-hydroxyindole
2,3-dimethyl-7-hydroxy-4-methoxyindole
5,6-dihydroxyindole
1-methyl-5,6-dihydroxyindole
2-methyl-5,6-dihydroxyindole
3-methyl-5,6-dihydroxyindole
2,3-dimethyl-5,6-dihydroxyindole
5-acetoxy-6-hydroxyindole
6acetoxy-5-hydroxyindole,
2-ethoxycarbonyl-5,6-dihydroxyindole
2-carboxy-5,6-dihydroxyindole
2,3-dimethyl-5-hydroxy-6-aminoindole
2,3-dimethyl-5-amino-6-hydroxyindole.

4. The process of claim 1 wherein said quinone derivative has formula II or formula III

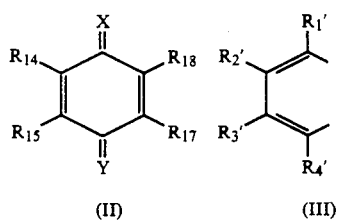

wherein

X represents oxygen or $NR_{19}$,

Y represents oxygen or $NR_{20}$, $R_{19}$ and $R_{20}$, each independently, represent hydrogen, halogen, $C_1$-$C_4$ alkyl, $C_1$-$C_4$ hydroxyalkyl, $C_1$-$C_4$ alkylsulphonyl or phenylsulphonyl, p1 $R_{14}$, $R_{15}$, $R_{16}$, $R_{17}$ and $R_{18}$, each independently, represent hydrogen; $C_1$-$C_4$ alkyl; carboxyl; $C_1$-$C_4$ alkylcarbonyl; $C_1$-$C_4$ alkoxycarbonyl; $C_1$-$C_4$ alkoxymethyl; $C_1$-$C_4$ alkylthiomethyl; $C_1$-$C_4$ hydroxyalkylthiomethyl; $C_1$-$C_4$ hydroxyalkylsulphinyl;

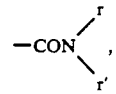

wherein r and R', each independently, represent hydrogen, or $C_1$-$C_4$ alkyl; carboxyalkyl; halogen; $C_1$-$C_4$ hydroxyalkyl; amino; amino substituted by one or two $C_{1-4}$ alkyl groups; amino substituted by one or two $C_1$-$C_4$ hydroxyalkyl groups; $C_2$-$C_6$ acylamin; $SO_3M$ wherein M represents hydrogen, K or Na; sulphoxide, sulphone; sulphonamide; $OZ_1$ wherein $Z_1$ represents hydrogen, $C_1$-$C_4$ alkyl, $C_1$-$C_4$ hydroxyalkyl, $C_1$-$C_4$ carboxyalkyl; carboxyphenyl; $C_4$ carboxyphenyl substituted by $C_1$-$C_4$ alkoxy; or —$SZ_2$ wherein $Z_2$ represents $C_1$-$C_4$ alkyl, $C_1$-$C_4$ hydroxyalkyl, $C_2$-$C_4$ dihydroxyalkyl or $C_1$-$C_4$ carboxyalkyl, or $R_{14}$ and $R_{15}$ form together with the carbon atoms to which they are attached a cyclic group having the formula

wherein $R'_1$, $R'_2$, $R'_3$ and $R'_4$ have the meanings given above for $R_{14}$, $R_{15}$, $R_{16}$, $R_{17}$ and $R_{18}$ when they do not form a ring.

5. The process of claim 1 wherein said quinone derivative is a benzoquinone having formula (II) or (II')

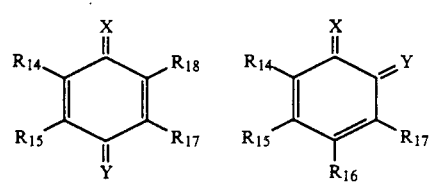

wherein

Rhd 14, $R_{15}$, $R_{16}$, $R_{17}$ and $R_{18}$, each independently, represent hydrogen; $C_1$-$C_4$ lower alkyl; $C_1$-$C_4$ lower alkoxy; halogen; $C_2$-$C_6$ acylamino; $SO_3M$ wherein M represents hydrogen, K or Na; $C_1$-$C_4$ alkoxy methyl; carboxy $C_1$-$C_4$ alkyl; $C_1$-$C_4$ alkoxycarbonyl; dialkylamino; $OZ_1$ wherein $Z_1$ represents carboxy $C_1$-$C_4$ alkyl or $C_1$-$C_4$ hydroxyalkyl; or $SZ_2$ wherein $Z_2$ represents $C_1$-$C_4$ hydroxyalkyl, $C_1$-$C_4$ dihydroxyalkyl, carboxy $C_1$-$C_4$ alkyl or $C_1$-$C_4$ alkyl;

X represents oxygen or $NR_{19}$,

Y represents oxygen or $NR_{20}$, $R_{19}$ and $R_{20}$, each independently, represent hydrogen, halogen, $C_1$-$C_4$ lower alkyl, methylsulphonyl or phenylsulphony.

6. The process of claim 1 wherein said quinone derivative has formula (V) or formula (VI)

wherein

R'₁, R'₂, R'₃, R'₄, R'₁₆, R₁₇ and R₁₈, each independently, represents hydrogen, $C_1$-$C_4$ alkyl, $C_1$-$C_4$ alkoxy; carboxyl; $C_1$-$C_4$ alkylcarbonyl; $C_1$-$C_4$ alkoxycarbonyl; $C_1$-$C_4$ alkoxymethyl; $C_1$-$C_4$ alkylthiomethyl; $C_1$-$C_4$ hydroxyalkylthiomethyl; $C_1$-$C_4$ hydroxyalkylsulphinyl;

$$-CON\begin{matrix}r\\ \\r'\end{matrix},$$

wherein r and r', each independently, represent hydrogen or $C_1$-$C_4$ alkyl; carboxyalkyl; halogen; $C_1$-$C_4$ hydroxyalkyl; amino; amino substituted by one or two $C_1$-$C_4$ alkyl groups; amino substituted by one or two $C_1$-$C_4$ hydroxyalkyl groups; $C_2$-$C_6$ acylamino; $SO_3M$ wherein M represents hydrogen, K or NA; dialkylamino; sulphoxide, sulphone; sulphonamide; $OZ_1$ wherein $Z_1$ represents hydrogen, $C_1$-$C_4$ alkyl, $C_1$-$C_4$ hydroxyalkyl, $C_1$-$C_4$ carboxyalkyl; carboxyphenyl; $C_4$ carboxyphenyl substituted by $C_1$-$C_4$ alkoxy; or —$SZ_2$ wherein $Z_2$ represents $C_1$-$C_4$ alkyl, $C_1$-$C_4$ hydroxyalkyl, $C_2$-$C_4$ dihydroxyalkyl or $C_1$-$C_4$ carboxyalkyl, X represents oxygen or $NR_{19}$, Y represents oxygen or $NR_{20}$ and $R_{19}$ and $R_{20}$, each independently, represent hydrogen, halogen, $C_1$-$C_4$ lower alkyl, methylsulphonyl or phenylsulphonyl.

7. The process of claim 1 wherein said quinone derivative is selected from the group consisting of
1,4-benzoquinone,
2-methoxy-1,4-benzoquinone,
2-methyl-1,4-benzoquinone,
2,6-dimethyl-1,4-benzoquinone,
2,3,5-trichloro-6-methyl-1,4-benzoquinone,
2-acetylamino-1,4-benzoquinone,
2-acetylamino-3,5-dimethyl-1,4-benzoquinone,
2,6-dimethyl-5acetylamino-1,4-benzoquinone,
2-chloro-1,4-benzoquinone,
tetrachloro-1,2-benzoquinone,
2,3-dimethoxy-1,4-benzoquinone,
2-β-carboxyethoxy-1,4-benzoquinone,
2-methoxymethyl-1,4-benzoquinone,
2-(βhydroxyethyl)-1,4-benzoquinone,
2-(βhydroxyethylthio)-1,4-benzoquinone,
2,5-bis(β-hydroxyethylthio)-1,4-benzoquinone,
2-(β,γ-dihydroxypropylthio)-1,4-benzoquinone,
2-(β-carboxyethylthio)-1,4-benzoquinone,
2-carboxymethyl-1,4-benzoquinone,
2-(β-hydroxyethylthio)-6-methyl-1,4-benzoquinone,
2-methoxycarbonyl-3-methoxy-1,4-benzoquinone,
2-methoxycarbonyl-1,4-benzoquinone,
2-methylthio-1,4-benzoquinone,
2-dimethylamino-1,4-benzoquinone,
2-acetylamino-5-methoxy-1,4-benzoquinone,
2-(β-hydroxyethylthio) methyl-1,4-benzoquinone,
2-(methylthio) methyl-1,4-benzoquinone,
4,5-dimethoxy-1,2-benzoquinone,
4-methyl-5-chloro-1,2-benzoquinone,
4,5-dimethyl-1,2-benzoquinone,
2,3-dimethyl-1,4benzoquinone,
2-β-hydroxyethoxy-1,4-benzoquinone,
N-methylsulphonyl-1,4-benzoquinone monoimine,
N-phenylsulphonyl-1,4-benzoquinone monoimine,
1,4-naphthoquinone,
1,2-naphthoquinone,
1,2-naphthoquinone-4-sulphonic acid
2,3-dichloro-1,4-naphthoquinone and
N-2,6-trichloro-1,4-benzoquinone imine.

8. The process of claim 1 wherein said composition A contains, 5,6-dihydroxyindole and said composition B contains a quinone derivative selected from the group consisting of
1,4-benzoquinone,
2-methyl-1,4-benzoquinone,
2,6-dimethyl-1,4-benzoquinone,
2-methoxy-1,4-benzoquinone,
2-chloro-1,4-benzoquinone,
2,3,5-trichloro-6-methyl-1,4-benzoquinone,
2-acetylamino-1,4-benzoquinone,
2-acetylamino-3-methoxy-1,4benzoquinone,
2,6-dimethyl-5-acetylamino-1,4-benzoquinone,
2,3-dimethoxy-1,4-benzoquinone,
2-methoxymethyl-1,4-benzoquinone,
2-(β-hydroxyethyl)-1,4-benzoquinone,
2-(β,γ-dihydroxypropylthio)-1,4-benzoquinone,
2-(β-carboxyethylthio)-1,4-benzoquinone,
2-carboxymethyl-1,4-benzoquinone,
1,4-naphthoquinone,
N-2,6-trichloro-1,4-benzoquinoneimine,
1,2-naphthoquinone and
1,2-naphthoquinone-4-sulphonic acid.

9. The process of claim 1 wherein said monohydroxyindole or dihydroxyindole is present in said composition A in an amount ranging from about 0.01 to 0.3 mole/liter.

10. The process of claim 1 wherein said quinone derivative is present in said composition B in an amount ranging from 0.005 to 1 mole/liter.

11. The process of claim 1 wherein the pH of said compositions A and B, each independently, ranges from 2 to 10.

12. The process of claim 1 wherein said composition B has an acidic pH.

13. The process of claim 1 wherein said cosmetically acceptable medium for said compositions A and B comprises water or a mixture of water and a cosmetically acceptable solvent.

14. The process of claim 1 wherein said cosmetically acceptable medium for said compositions A and B comprises a cosmetically acceptable anhydrous solvent containing less than 1% water.

15. The process of claim 1 wherein said compositions A and B, each independently, also contain an anionic, cationic, nonionic or amphoteric surfactant or a mixture thereof; a thickener; a fragrance; a sequestering agent; a film-forming agent; a treatment agent; a dispersing agent; a conditioner; a preservative; an opacifying agent; or a swelling agent for keratinous fibers.

16. The process of claim 1 wherein said composition A or said composition B or both said compositions also contains another dye selected from a direct dye, an oxidation dye, a coupler or a rapid oxidation dyestuff precursor having a benzenic structure and generating a colored compound when oxidized in air.

17. The process of claim 1 wherein said composition A or said composition B or both said compositions also contains another quinone dye selected from the group consisting of a benzoquinone dye, a benzoquinoneimine dye, a benzoquinonediimine dye, a naphthoquinone dye, a naphthoquinoneimine dye, a naphthoquinonediimine dye and a quinone indole dye, said another quinone dye having an oxidation-reduction potential such that $\Delta E$ is greater than 320 mV.

18. A multicompartment kit for use in dyeing keratinous fibers comprising a first compartment housing said composition A defined in claim 1 and a second compartment housing said composition B defined in claim 1.

19. A multicompartment kit for use in dyeing keratinous fibers comprising a first compartment housing said composition A defined in claim 1, a second compartment housing said composition B defined in claim 1, wherein the said cosmetically acceptable medium of at least one of said compositions A and B comprises a cosmetically acceptable anhydrous solvent, and a third compartment housing a cosmetically acceptable aqueous medium to be admixed just before use with contents of said compartment containing one or the other of said compositions A and B in said cosmetically acceptable anhydrous solvent.

* * * * *